United States Patent [19]
Bueche et al.

[11] Patent Number: 6,053,858
[45] Date of Patent: Apr. 25, 2000

[54] RADIATION SOURCE

[75] Inventors: Kenneth M. Bueche, Friendswood; Anthony J. Bradshaw, Missouri City; Richard T. Thornton, League City, all of Tex.

[73] Assignee: Advanced Cardiovascular Systems, Inc., Santa Clara, Calif.

[21] Appl. No.: 09/090,892

[22] Filed: Jun. 4, 1998

[51] Int. Cl.[7] ..................................................... A61N 5/00
[52] U.S. Cl. ................................................................. 600/3
[58] Field of Search ............................................. 600/1–8

[56] References Cited

U.S. PATENT DOCUMENTS

| | | | |
|---|---|---|---|
| 4,861,520 | 8/1989 | van't Hooft et al. | 600/8 |
| 5,176,617 | 1/1993 | Fischell et al. | 600/3 |
| 5,575,749 | 11/1996 | Liprie | 600/3 |
| 5,833,593 | 11/1998 | Liprie | 600/3 |
| 5,871,436 | 2/1999 | Eury | 600/3 |

*Primary Examiner*—John P. Lacyk
*Attorney, Agent, or Firm*—Blakely, Sokoloff, Taylor & Zafman LLP

[57] ABSTRACT

A radiation source for invasive medical treatment, such as intracoronary radiotherapy or other such intravascular radiotherapy, is described. The radiation source includes a thread extending longitudinally within a sleeve. The sleeve is a hollow circular cylinder, sealed at either end, made from a polyimide resin, and is configured such that it is sufficiently flexible enough to be used for intravascular radiotherapy. A plurality of laser-drilled holes are configured in an evenly spaced pattern along the sleeve, and promote uniform liquid evaporation from within the sleeve. The thread is comprised of twelve rayon filaments wound in a helical fashion, which extend longitudinally through the sleeve and are anchored in the seals at either end of the sleeve. A radioactive isotope is formed into a coating on surfaces within the sleeve. The coating is formed by introducing a drop of a liquid-borne radioactive isotope into contact with the sleeve such that capillary forces distribute the liquid throughout the sleeve, and evaporating the liquid to form a uniform plating of the isotope within the sleeve. The sleeve and thread include a coating of a surfactant to promote capillary action during the distribution of the liquid throughout the sleeve. During the formation of the sleeve, the sleeve and thread are wet and then dried, preshrinking them so as to avoid the sleeve's warping during later use.

54 Claims, 2 Drawing Sheets

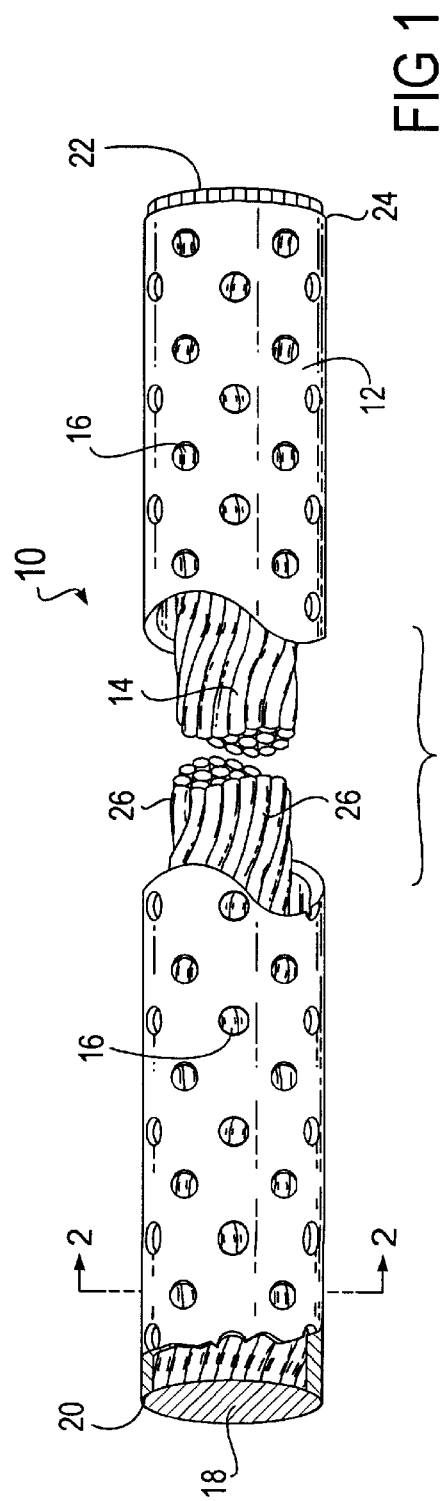
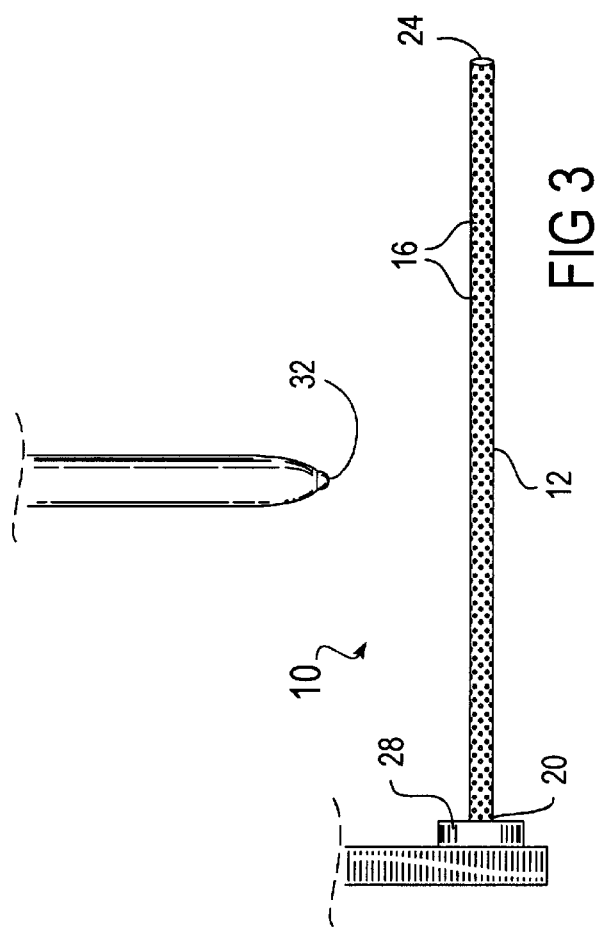
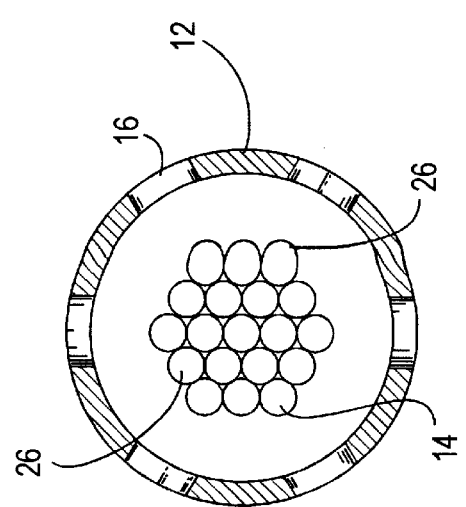

RADIATION SOURCE

BACKGROUND OF THE INVENTION

This invention relates generally to invasive medical radiotherapy and, more particularly, to a radiation source for use in invasive medical treatment, and to a method for making it.

Physicians now use radiation to treat an increasing number of medical problems. One form of radiation treatment involves the insertion of a radiation source into a patient's body to irradiate a limited area of the body for a controlled period of time. Typically, a surgeon inserts a longitudinal radiation source into the patient's body through a lumen of an implanted guide catheter. This procedure often requires a radiation source to exhibit both high flexibility and an effectively high level of radioactivity, particularly for cardiovascular radiotherapy. Furthermore, the radiation source must provide consistent levels of radiation over its entire length.

During implantation, the radiation source might be required to travel through tortuous pathways within a patient's body, such as the coronary arteries. Furthermore, the area requiring treatment might be characterized by tortuous twists and bends. A radiation source must therefore be sufficiently flexible to navigate such pathways without injuring the patient or damaging itself.

Once the radiation source has been inserted into the patient's body, the total dosage of radiation will be determined by the level of radioactivity of the radiation source, and by the length of time the targeted tissue is exposed to the radiation source. Radiation sources having higher radiation levels provide for shorter exposure times, which lowers both the time duration of a procedure and the level of risk involved in the procedure. This risk is particularly important in situations where the guide catheter causes significant obstruction to the profusion of the blood. However, existing technologies provide for higher levels of radioactivity at the expense of flexibility, thus placing an upper limit on the radiation levels available for treating tortuous pathways.

A limiting factor on the design of such radiation sources is the risk of overexposing a patient to radiation due to inconsistent levels of radiation along the length of the radiation source. The radiation source is brought into close proximity with portions of the patient's body, and a particularly "hot" portion of the radiation source can therefore overexpose an adjacent portion of the patient's body. Likewise, longitudinal sections having a lower than desired radiation level can provide lower than desired levels of radiation treatment. Thus, the radiation level along a radiation source must be kept as longitudinally consistent as possible. It is known that longitudinal uniformity is important, and that a preferred level of uniformity is a maximum 10% variation.

It is known, for example, that a radiation source can be formed in a cavity within a wire or within a tube (also known as a ribbon), and can include a plurality of rigid pellets, made from a radioactive isotope, that are embedded at intervals along the wire with spacers positioned between the pellets. The spacers function to give this source wire some flexibility despite the presence of the rigid pellets. The flexibility is restricted, however, to the areas between the pellets. Furthermore, the pellets form a series of nonuniform radiation hot spots, causing tissue around the source wire to be irradiated unevenly. Longer spacers improve the source wire's flexibility, however they cause the distribution of radiation to be less uniform and less continuous, and thus a trade off must be made between flexibility and radiation uniformity.

It has been suggested that an isotope could be carried in a liquid, and passed into, and then out of a passage in a catheter. However, when the catheter assumes a strongly bent position, such as in a tortuous passage, a portion of the passage could change in cross-sectional shape, and the quantity of the isotope that could be located in that portion would vary. Thus, the catheter would have local radiation levels that vary with the bent shape of the catheter, and would not maintain a uniform radiation level distribution.

Accordingly, there has existed a definite need for an invasive medical treatment radiation source, where the radiation source exhibits high flexibility and high levels of radioactivity, the radioactivity being distributed in a uniform and continuous fashion throughout the radiation source. The present invention satisfies these and other needs, and provides further related advantages.

SUMMARY OF THE INVENTION

The present invention provides a radiation source for invasive medical treatment, where the radiation source exhibits high flexibility and high levels of radioactivity, the radioactivity being distributed in a uniform and continuous fashion throughout the radiation source, and a method of making the radiation source. The present invention further provides a related method of employing the radioactive isotope for invasive medical treatment. The invention has potential use in a wide range of applications, such as intravascular radiotherapy and oncology.

A radiation source for invasive medical treatment, embodying the present invention, features a hollow sleeve (e.g., a tube or cylinder) and a coating of a radioactive isotope distributed on surfaces in the interior of the sleeve. This radiation source provides for the irradiation of tissue, within a patient's body, along long and tortuously curved pathways in the body, such as coronary arteries. It further provides for a substantially even level of irradiation along the full length of irradiated tissue.

The invention also features a structure, e.g., a thread with filaments wound in a helical pattern, within the sleeve, that is configured to distribute a liquid throughout the sleeve by capillary action. This feature advantageously provides for the uniform spreading of the isotope, while born in a liquid, throughout the sleeve. The structure preferably extends from a first seal at a first end of a sleeve, to a second seal at a second end of the sleeve. The helical filaments may cause the thread to follow a pig-tailed, coiled path down the sleeve. The thread and seals promote even capillary spreading of the liquid, providing even distribution of a liquid-born isotope, and thus serving as a further means for distributing the liquid-born isotope throughout the sleeve. The pig-tailed thread may further enhance the capillary action.

A further feature of the invention is that the sleeve is configured to promote liquid evaporation from within the sleeve at a consistent rate throughout the sleeve. This feature can comprise a plurality of holes in the sleeve, which are positioned at approximately equal intervals along the sleeve's length and spaced at approximately symmetric locations around the sleeve's circumference. The holes can be any form of orifice, such as circular or oval openings, slits that open under internal pressure, or even the pores in a porous material having large enough pores to allow evaporation. This feature advantageously allows for the uniform evaporation, along the length of the sleeve, of a liquid that bears the isotope. The evaporation causes the surfaces distributed throughout the interior of the sleeve to be plated with a uniform coating of the precipitated isotope.

Additionally, the invention features a coating of a surfactant along surfaces in the interior of the sleeve. The surfactant reduces surface tension of the fluid, to promote uniform spreading of a liquid throughout the sleeve, through capillary action.

Other features and advantages of the invention will become apparent from the following detailed description of the preferred embodiments, taken in conjunction with the accompanying drawings, which illustrate, by way of example, the principles of the invention.

BRIEF DESCRIPTION OF THE DRAWINGS

FIG. 1 is an elevational view of a source configured to receive a radioactive isotope, embodying features of the present invention.

FIG. 2 is a cross-sectional side view of the source depicted in FIG. 1, taken along line 2—2 of FIG. 1.

FIG. 3 is an elevational view of the source depicted in FIG. 1, being held in a device configured to hold the source, the source being in the process of contacting a drop of a liquid-borne radioactive isotope.

DETAILED DESCRIPTION OF THE PREFERRED EMBODIMENTS

Figure 4:
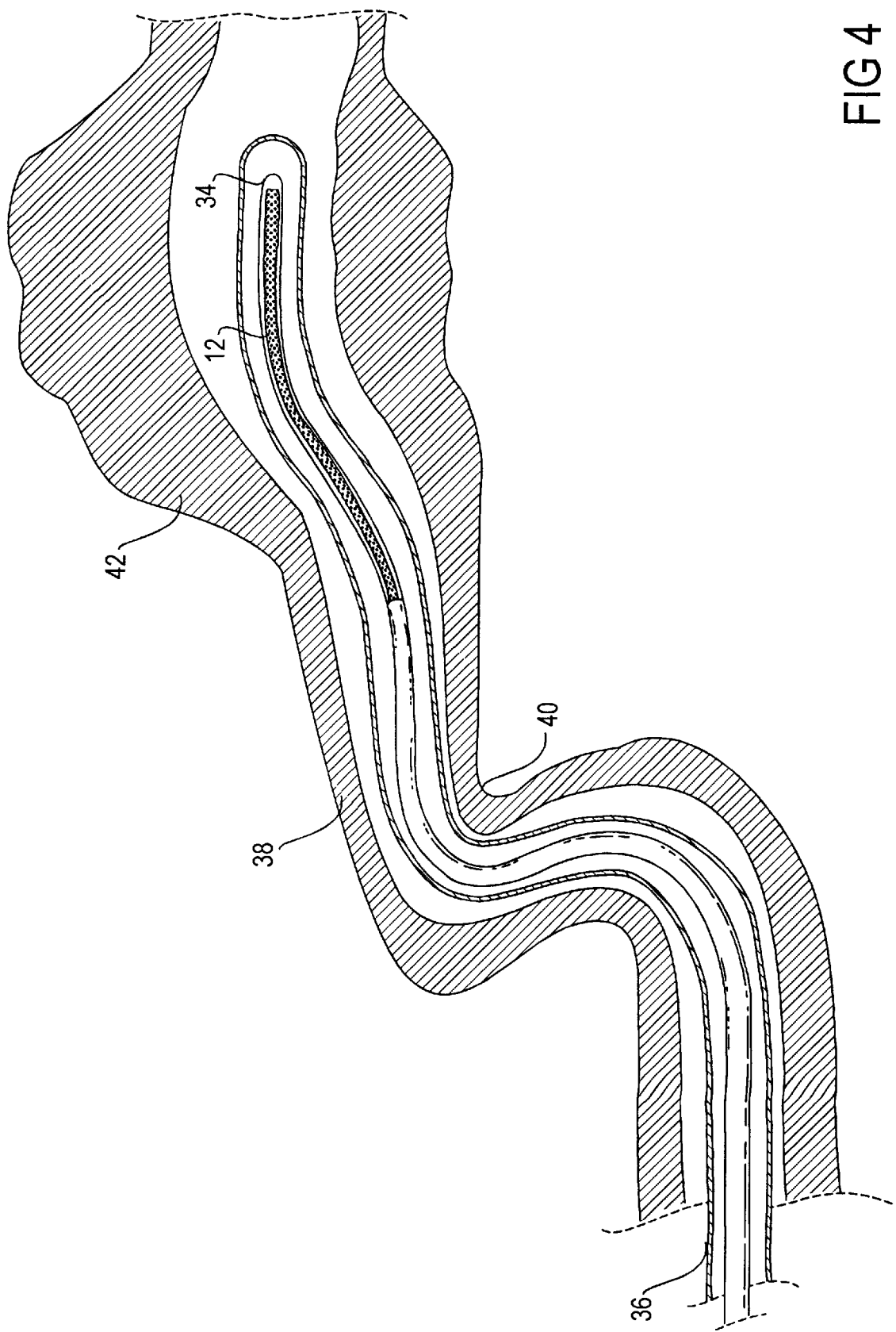
FIG. 4 is an elevational view of the source depicted in FIG. 1, inserted in a patient's cardiovascular system through a guide catheter for cardiovascular radiotherapy.

With reference now to the illustrative drawings, and particularly to FIGS. 1 and 2, there is shown one embodiment of a "source" 10 configured to receive a radioactive isotope for invasive medical treatment, such as intracoronary radiotherapy, or other such intravascular radiotherapy, according to the present invention. The source includes a foundation, preferably in the form of a hollow sleeve 12, and most preferably including a thread 14 extending longitudinally within the sleeve. This foundation includes surfaces for receiving a coating of a radioactive isotope. Preferably, the isotope is precipitated from an evaporating liquid and plated onto the surfaces. The sleeve and thread provide capillary forces to draw a drop of liquid-borne radioactive isotope into the sleeve and distribute it throughout the sleeve, such that it plates on surfaces within the sleeve.

The sleeve 12 is preferably in the form of a hollow circular cylinder, defining a longitudinal axis. The sleeve is preferably made from a polyimide resin, or other such elastic material that is resistant to radiation degradation. The diameter and wall thickness of the sleeve are selected to be sufficiently flexible for intravascular radiotherapy. Preferably, the sleeve's length is substantially greater than its diameter to provide for irradiation of an extended length of tissue in a narrow vessel. For example, the sleeve's length might be greater than 1 inch, while the sleeve's diameter is less than 0.02 inches.

The hollow sleeve 12 defines a plurality of holes 16 connecting the interior surface of the sleeve to the exterior surface of the sleeve. The holes, in groups of six, are longitudinally spaced at equal intervals along the length of the sleeve. Each group of six holes is symmetrically spaced around the circumference of the sleeve at a given longitudinal location. Longitudinally consecutive groups of holes are circumferentially offset by 30° from each other. The holes are configured in an evenly spaced pattern that promotes liquid evaporation from within the sleeve at a reasonably consistent rate throughout the length and circumference of the sleeve. Thus, the holes provide a means of coating surfaces throughout the interior of the sleeve with a substantially uniform plating of the isotope, such that the sleeve is appropriate for evenly irradiating nearby tissue.

A first seal 18 caps the sleeve 12 at a first end 20, preferably sealing that end to prevent liquid flow through that end. A second seal 22 caps the sleeve at a second end 24, preferably sealing that end to prevent liquid flow through that end. The seals, like the sleeve, are preferably made from a polyimide resin. The thread 14 includes two ends, which are anchored in the two seals, respectively. The seals thus maintain the ends of the thread in alignment with the capped ends of the sleeve, and prevent liquid flow through those ends.

The thread 14 extends longitudinally through the sleeve 12 from the sleeve's first end 20 to its second end 24. The longitudinal cross-section of the thread (see FIG. 2) defines an area that is preferably consistent along the length of the thread, preferably filling roughly 25% to 30% of the sleeve's volume. The thread 14 is preferably comprised of approximately twelve rayon filaments 26 wound in a helical fashion, as depicted in FIG. 1. Thread of this nature can be found as strands within larger threads.

While this embodiment includes a thread 14, other embodiments can be provided with other alternative structures within the sleeve, such as a unitary thread or a rigid structure. These structures preferably provide for the distribution of a liquid throughout the sleeve, such as by capillary forces. These structures also preferably provide plating surfaces throughout the sleeve that are configured for a predetermined distribution of precipitated isotope. Preferably, the predetermined distribution of the isotope is an approximately uniform distribution along the length of the sleeve.

Both the sleeve 12 and the thread 14 include a coating of a surfactant, such as Pluronic Surfactant type 68, manufactured by BASF. The surfactant lowers surface tension of a liquid within the sleeve, promoting uniform spreading of the liquid throughout the sleeve by capillary action.

The invention includes a related method of employing a radioactive isotope for invasive medical treatment. In this inventive method, the sleeve 12 is formed in its desired diameter and thickness. Laser drilling is preferably used to form the holes 16 in the sleeve.

The thread 14 is inserted into the sleeve 12, and the first seal 18 is formed, anchoring the first end of the thread to the first end 20 of the sleeve. The first seal is formed by heating the end of the sleeve and thread to approximately 80° C. to 100° C., preferably in a column of heated gas, to solidify the ends of the sleeve and thread into a unitary seal. Prior to insertion, the thread may be passed through a drop of adhesive in order to stiffen it, easing the its insertion into the sleeve 12.

With only one seal formed, the sleeve 12 and thread 14 are wet (preferably by dunking in water) and then dried. This wetting and drying preshrinks the thread prior to forming the second seal 22, and thus avoids potential warping during later steps of the process.

The second seal 22 is then formed, anchoring the second end of the thread 14 to the second end 24 of the sleeve 12. As with the first seal, the second seal is formed by heating the end of the sleeve and thread, preferably in a column of heated gas, to solidify the ends of the sleeve and thread into a unitary seal.

The sleeve and the thread are then wet (preferably by dunking) with a surfactant. The surfactant is dried to complete the formation of the source. The surfactant, coating surfaces within the sleeve, promotes capillary action within the sleeve. This is particularly important in low humidity environments when static electricity might be a problem.

To plate a coating of a radioactive isotope on the surfaces within the sleeve 12, the radioactive isotope is provided while borne in a liquid. The radioactive isotope is preferably Phosphorus-32 (P-32), which has a high specific activity, and the liquid is preferably water. While a number of Phosphorus-32 radionuclide solutions may be used, preferably the solution is radioactive orthophosphoric acid ($H_3PO_4$) in water. The provision of a highly concentrated liquid-borne radioactive isotope allows a higher level of radioactivity per unit of liquid, and thus produces a radiation source with higher levels of radiation.

Referring now to FIGS. 1 to 3, the first end 20 of the completed radiation source's sleeve 12 is placed into a retaining device 28, which holds the source without covering a significant number of the source's holes 16. The retaining device is preferably configured with a hollow cylinder having an inner diameter conforming to the outer diameter of the sleeve, providing for a friction grip on the source.

The source 10, held by the retaining device 28, is brought into contact with the liquid-borne radioactive isotope. Preferably, the source is positioned below a drop 32 of the liquid-borne radioactive isotope, and is moved up into contact with the drop. The drop contacts the source in the source's central portion, between the ends 20, 24 of the sleeve 12, and most preferably at the approximate longitudinal midpoint of the sleeve. The drop is preferably of a correct volume to approximately fill the sleeve. The drop is preferably suspended from a syringe. A preferred apparatus, including a syringe and a retaining device 28, for use with the invention is described in the concurrently filed and commonly assigned patent application, entitled METHOD AND APPARATUS FOR CONCENTRATING A SOLUTE IN SOLUTION WITH A SOLVENT, having application Ser. No. 09/090,891, which is incorporated herein by reference.

Upon contact, the drop 32 of the liquid-borne radioactive isotope enters the sleeve 12 through the holes 16. As the drop enters the sleeve, capillary forces draw the liquid from the middle of the sleeve to the ends 20, 24 of the sleeve, spreading the drop uniformly throughout the sleeve. Both the thread 14 and the coating of surfactant encourage the capillary action, improving the distribution of the liquid.

The source 10, containing the drop of liquid, is heated to cause the evaporation of the liquid. The heat can optionally be provided by the same heat source that was used to form the seals 18, 22 at the ends of the sleeve 12. The evaporating liquid leaves a radioactive precipitated isotope residue plated within the sleeve, completing the radiation source.

The thread 14 and the sleeve 12 have consistent surfaces throughout the interior of the sleeve, providing for a consistent volume of the liquid throughout the sleeve, and thus providing for uniform plating of the precipitated isotope. The uniformly spaced holes 16, and the watertight seals 18, 22 further encourage uniformity in the plating of the precipitated isotope. While heating the source is the preferred method of evaporation, other methods can be used. For example, altering the air pressure, or even leaving the source exposed to the unaltered atmosphere, would be alternate methods of evaporating the liquid.

As seen in FIG. 4, the completed radiation source, comprising the sleeve 12 and its contents, is then sealed within a cavity in a wire 34, using a water-tight seal, to create a radiation source wire. The source wire is subsequently inserted into a guide catheter 36, which is positioned within a cardiovascular vessel 38 in a patient's body. Because the radiation source is highly flexible, it can pass through, and be positioned in tortuous regions 40 of the vessel, to irradiate the tissue 42 to be treated. The positioned radiation source thus employs a radioactive isotope for invasive medical treatment.

The sealed source wire 34 provides a mechanism to quickly and safely insert and locate the radiation source through a guide catheter 36 within a patient's body. The watertight seal protects the patients body from direct contact with the isotope. Additional safety is gained by the isotope's being plated on surfaces in the interior of the sleeve 12, and thus not being prone to leaking out. This protection is in addition to the protection provided by the guide catheter, which typically isolates a patient's body from radiation sources.

While the above method of employing a radioactive isotope for invasive medical treatment is preferable, other methods are within the scope of the invention. For example, the source can be formed with only one end of the sleeve sealed, and the drop can first contact the thread or the sleeve at the other end of the sleeve. Such an arrangement might be advantageous if the liquid-borne isotope is provided in a container, and is not conveniently dispensed in drops.

Furthermore, it would be within the scope of the invention to use structures other than the thread to encourage the liquid to wick, under capillary forces, throughout the sleeve. Indeed, the invention can be practiced without the thread or the seals, however it might be more difficult to obtain uniform distribution of the isotope in such embodiments.

An alternate method of treating a patient, which is within the scope of the present invention, includes providing the radiation source, sealing the radiation source within a water tight capsule, and implanting the capsule into the patient's body. This method would generally be more appropriate for a radiation source having very low levels of radiation, or possibly having an isotope with a short half-life.

From the foregoing description, it will be appreciated that the present invention provides a source configured to receive a radioactive isotope, forming a radiation source for invasive medical treatment. It further provides a related method of employing a radioactive isotope for invasive medical treatment. The radiation source is flexible, and can carry a radioactive isotope having a high level of radioactivity distributed uniformly along its length.

While a particular form of the invention has been illustrated and described, it will be apparent that various modifications can be made without departing from the spirit and scope of the invention. Thus, although the invention has been described in detail with reference only to the preferred embodiments, those having ordinary skill in the art will appreciate that various modifications can be made without departing from the invention. Accordingly, the invention is not intended to be limited, and is defined with reference to the following claims.

We claim:

1. A housing for carrying a radioactive isotope, comprising:
    a hollow longitudinal sleeve; and
    a structure, within the sleeve configured to distribute a liquid longitudinally throughout the sleeve by capillary action.

2. The housing of claim 1, wherein the sleeve is configured to promote liquid evaporation from within the sleeve at a consistent rate longitudinally throughout the sleeve.

3. The housing of claim 2, and further comprising a first seal at a first end of the sleeve.

4. The housing of claim 3, and further comprising a second seal at a second end of the sleeve.

5. The housing of claim 2, wherein the sleeve's configuration to promote liquid evaporation comprises a plurality of holes defined in the sleeve.

6. The housing of claim 5, wherein the plurality of holes are openings positioned at approximately equal intervals longitudinally along the sleeve, and wherein the plurality of holes are spaced at approximately symmetric locations around the circumference of the sleeve.

7. The housing of claim 6, and further comprising a first seal at a first end of the sleeve and a second seal at a second end of the sleeve.

8. The housing of claim 1, wherein the structure configured to distribute the liquid is a thread extending longitudinally within the sleeve.

9. The housing of claim 8, wherein the thread includes a plurality of filaments.

10. The housing of claim 9, wherein the thread is anchored to a first end of the sleeve, and the thread is anchored to a second end of the sleeve.

11. The housing of claim 10, wherein the plurality of filaments extend along the sleeve in a helical configuration.

12. The housing of claim 8, wherein the lengths of the thread and the sleeve are substantially longer that the diameter of the sleeve, and wherein the thread and the sleeve are sufficiently flexible to be used in intracoronary radiotherapy.

13. The housing of claim 1, wherein the housing includes one or more surfaces within the sleeve, the surfaces being coated with a surfactant.

14. The housing of claim 1, and further comprising:
a first seal at a first end of the sleeve; and
a second seal at a second end of the sleeve;
wherein the sleeve defines a plurality of holes to promote liquid evaporation from within the sleeve at a consistent rate longitudinally throughout the sleeve;
wherein the plurality of holes are openings positioned at approximately equal intervals longitudinally along the sleeve;
wherein the plurality of holes are spaced at approximately symmetric locations around the circumference of the sleeve;
wherein the structure configured to distribute the liquid is a thread extending longitudinally within the sleeve, the thread including a plurality of filaments;
wherein the first seal anchors the thread to the second end of the sleeve;
wherein the second seal anchors the thread to the second end of the sleeve; and
wherein the thread and the sleeve are sufficiently flexible to be used in intracoronary radiotherapy.

15. A radiation source for invasive medical treatment, comprising:
a longitudinal foundation; and
a coating of a radioactive isotope formed on the foundation by an evaporating liquid.

16. The radiation source of claim 15, wherein:
the foundation is a hollow longitudinal sleeve; and
the coating of the radioactive isotope is plated on surfaces in the interior of the sleeve by the evaporating liquid.

17. The radiation source of claim 16, wherein the sleeve is configured to promote liquid evaporation from within the sleeve at a consistent rate longitudinally throughout the sleeve.

18. The radiation source of claim 17, wherein the sleeve defines a plurality of holes to promote evaporation.

19. The radiation source of claim 17, and further comprising a first seal at a first end of the sleeve, and a second seal at a second end of the sleeve.

20. The radiation source of claim 16, and further comprising a structure, within the sleeve, configured to distribute the evaporating liquid longitudinally throughout the sleeve by capillary action.

21. The radiation source of claim 20, wherein the structure configured to distribute the evaporating liquid is a thread extending longitudinally within the sleeve, the thread including a plurality of filaments.

22. The radiation source of claim 21, wherein the thread is anchored to a first end of the sleeve and to a second end of the sleeve, and wherein the plurality of filaments extend along the sleeve in a helical configuration.

23. The radiation source of claim 21, wherein the length of the sleeve is substantially longer than the diameter of the sleeve, and wherein the thread is sufficiently flexible to be used in intracoronary radiotherapy.

24. The radiation source of claim 16, and further comprising:
a thread extending longitudinally within the sleeve, the thread including a plurality of filaments extending along the sleeve in a helical configuration, the thread being configured to distribute the evaporating liquid longitudinally throughout the sleeve by capillary action; and
a first seal anchoring the thread at a first end of the sleeve, and a second seal anchoring the thread at a second end of the sleeve;
wherein the sleeve defines a plurality of holes to promote liquid evaporation from within the sleeve at a consistent rate longitudinally throughout the sleeve;
wherein the plurality of holes are opening positioned at approximately equal intervals longitudinally along the sleeve;
wherein the lengths of the thread and the sleeve are substantially longer than the diameter of the sleeve; and
wherein the thread and the sleeve are sufficiently flexible to be used in intracoronary radiotherapy.

25. The radiation source of claim 15, and further comprising a wire containing the foundation in a cavity within the wire, wherein the wire provides a watertight seal around the foundation.

26. The radiation source of claim 25, wherein:
the foundation is a hollow longitudinal sleeve; and
the coating of a radioactive isotope is plated on surfaces in the interior of the sleeve by the evaporating liquid.

27. The radiation source of claim 26, and further comprising a first seal at a first end of the sleeve, and a second seal at a second end of the sleeve, wherein the sleeve defines a plurality of holes to promote liquid evaporation from within the sleeve.

28. The radiation source of claim 26, and further comprising a thread extending longitudinally within the sleeve, configured to distribute the evaporating liquid throughout the sleeve by capillary action, wherein the thread is anchored to a first end of the sleeve and to a second end of the sleeve.

29. The radiation source of claim 26, and further comprising:
a thread extending longitudinally within the sleeve, configured to distribute the evaporating liquid longitudinally throughout the sleeve by capillary action, the thread including a plurality of filaments extending along the sleeve in a helical configuration;

a first seal anchoring the thread at a first end of the sleeve; and a second seal anchoring the thread at a second end of the sleeve;

wherein the sleeve defines a plurality of holes to promote liquid evaporation from within the sleeve; and wherein the thread and the sleeve are sufficiently flexible to be used in intracoronary radiotherapy.

30. The radiation source of claim 15, wherein the radioactive isotope is Phosphorus-32.

31. A method of manufacture a radiation source for invasive medical treatment, comprising:

providing a longitudinal foundation; and coating the foundation with a precipitated radioactive isotope.

32. The method of claim 31, wherein:

the provided foundation is a hollow longitudinal sleeve; and the step of coating the foundation includes coating surfaces distributed longitudinally throughout in the interior of the sleeve with the precipitated isotope.

33. The method of claim 32, and further comprising sealing the sleeve, coated with the isotope, within a cavity in a wire, using a water-tight seal.

34. The method of claim 32, wherein the step of coating with the isotope includes contacting the isotope, borne in a liquid, with the sleeve, such that capillary action will longitudinally distribute the liquid-borne isotope throughout the sleeve, and wherein the step of coating with the isotope further includes evaporating the liquid to cause plating of the isotope within the sleeve.

35. The method of claim 34, wherein the isotope, borne in a liquid, is radioactive orthophosphoric acid in water.

36. The method of claim 34, and further comprising coating surfaces in the interior of the sleeve with a surfactant prior to the step of contacting the isotope with the sleeve.

37. The method of claim 34, wherein the sleeve defines a plurality of holes to promote liquid evaporation from within the sleeve.

38. The method of claim 37, wherein the sleeve includes a first seal at a first end of the sleeve and a second seal at a second end of the sleeve, and wherein the sleeve contacts the liquid-borne isotope with a central portion of the sleeve.

39. The method of claim 34, and further providing a thread extending longitudinally within the sleeve.

40. The method of claim 39, and further comprising:

anchoring the thread to a first end of the sleeve;

wetting and drying the thread to preshrink the thread; and anchoring the preshrunk thread to a second end of the sleeve;

wherein the thread includes a plurality of filaments extending along the sleeve in a helical configuration; and wherein the sleeve defines a plurality of holes to promote liquid evaporation from within the sleeve.

41. The method of claim 40, and further comprising:

laser drilling a plurality of holes in the sleeve to promote liquid evaporation from within the sleeve;

providing a thread extending longitudinally within the sleeve, wherein the lengths of the thread and the sleeve are substantially longer than the diameter of the sleeve, and wherein the thread and the sleeve are sufficiently flexible to be used in intracoronary radiotherapy; and coating surfaces in the interior of the sleeve with a surfactant prior to the step of contacting the isotope with the sleeve;

wherein the step of anchoring the thread to the first end of the sleeve includes providing the sleeve with a first seal that anchors the thread, wherein the step of anchoring the thread to the second end of the sleeve includes providing the sleeve with a second seal that anchors the thread; and wherein the liquid-borne isotope contacts a central portion of the sleeve in the step of contacting the isotope with the sleeve.

42. The method of claim 41, wherein the lengths of the thread and the sleeve are substantially longer than the diameter of the sleeve, and wherein the thread and the sleeve are sufficiently flexible to be used in intracoronary radiotherapy.

43. The method of claim 31, wherein the isotope, borne in a liquid, is a Phosphorus-32 radionuclide solution.

44. A radiation source employing a radioactive isotope for invasive medical treatment, comprising:

a hollow sleeve; and means for coating surfaces throughout in the interior of the sleeve with a precipitated radioactive isotope.

45. The radiation source of claim 44, wherein the means for coating includes a means for distributing a liquid-borne isotope throughout the sleeve.

46. The radiation source of claim 44, wherein the means for coating includes a means for evaporating a liquid-borne isotope within the sleeve to cause the plating of the isotope.

47. The radiation source of claim 44, wherein the means for coating includes a means for reducing surface tension to promote uniform spreading of a liquid longitudinally throughout the sleeve, through capillary action.

48. A method of employing a radioactive source for invasive medical treatment, comprising:

providing a longitudinal foundation;

coating the foundation with a precipitated radioactive isotope; and inserting the foundation, coated with the precipitated isotope, into a patient's body.

49. The method of claim 48, wherein:

the provided foundation is a hollow longitudinal sleeve; and the step of coating the foundation includes coating surfaces distributed longitudinally throughout the interior of the sleeve with the precipitated isotope.

50. The method of claim 49, wherein the step of coating with the isotope includes contacting the isotope, borne in a liquid, with the sleeve, such that capillary action will distribute the liquid-borne isotope throughout the sleeve; and evaporating the liquid to cause plating of the isotope within the sleeve.

51. The method of claim 49, and further comprising coating surfaces in the interior of the sleeve with a surfactant prior to the step of contacting the isotope with the sleeve, wherein the provided sleeve defines a plurality of holes to promote liquid evaporation from the sleeve.

52. The method of claim 49, wherein the sleeve includes a first seal at a first end of the sleeve and a second seal at a second end of the sleeve, and wherein the sleeve contacts the liquid-borne isotope with a central portion of the sleeve.

53. The method of claim 49, and further comprising:

providing a thread extending longitudinally within the sleeve;

anchoring the thread to a first end of the sleeve;

preshrinking the thread; and anchoring the preshrunk thread to a second end of the sleeve;

wherein the thread includes a plurality of filaments extending along the sleeve in a helical configuration.

54. The method of claim 49, and further comprising sealing the sleeve, coated with the isotope, within a cavity in a wire, using a water-tight seal.

* * * * *